US012629020B2

(12) United States Patent
Meyer et al.

(10) Patent No.: US 12,629,020 B2
(45) Date of Patent: May 19, 2026

(54) ARRANGEMENT AND METHOD FOR MEASURING A FIELD OF VISION AND USE OF AN IMPLANT

(71) Applicant: Implandata Ophthalmic Products GMBH, Hannover (DE)

(72) Inventors: Stefan Meyer, Hannover (DE); Max Ostermeier, Seevetal (DE)

( * ) Notice: Subject to any disclaimer, the term of this patent is extended or adjusted under 35 U.S.C. 154(b) by 782 days.

(21) Appl. No.: 17/629,683

(22) PCT Filed: Jul. 21, 2020

(86) PCT No.: PCT/EP2020/070517
§ 371 (c)(1),
(2) Date: Jan. 24, 2022

(87) PCT Pub. No.: WO2021/013821
PCT Pub. Date: Jan. 28, 2021

(65) Prior Publication Data
US 2022/0240776 A1      Aug. 4, 2022

(30) Foreign Application Priority Data

Jul. 23, 2019      (DE) ......................... 102019119913.1

(51) Int. Cl.
*A61B 3/10*          (2006.01)
*A61B 3/02*          (2006.01)
(Continued)

(52) U.S. Cl.
CPC ................ *A61B 3/113* (2013.01); *A61B 3/16* (2013.01); *G16H 50/30* (2018.01); *A61B 2562/0219* (2013.01)

(58) Field of Classification Search
CPC ......... A61B 3/02; A61B 3/102; A61B 3/1025; A61B 3/113; A61B 3/005; A61B 3/1225;
(Continued)

(56) References Cited

U.S. PATENT DOCUMENTS

| 5,920,375 | A | * | 7/1999 | Fahle | ..................... | A61B 3/024 |
| | | | | | | 351/224 |
| 2005/0165302 | A1 | * | 7/2005 | Oeltermann | ........... | A61B 3/113 |
| | | | | | | 600/421 |

(Continued)

FOREIGN PATENT DOCUMENTS

| CN | 102711594 A | 10/2012 |
| CN | 103458775 A | 12/2013 |

(Continued)

OTHER PUBLICATIONS

International Search Report, application No. PCT/EP2020/070517, issued Jul. 21, 2020, p. 7.

(Continued)

*Primary Examiner* — Dawayne Pinkney
(74) *Attorney, Agent, or Firm* — Jason Plotkin

(57) ABSTRACT
To specify an arrangement and a method for measuring a field of vision of an eye (6) which, while avoiding the disadvantages of the prior art, enable an objective, less complex and more reliable measurement of a field of vision of an eye (6), it is proposed that the arrangement comprises measuring means (1, 3) for measuring an eye movement and in the method, the eye movement is measured in an initial measurement (S1). Furthermore, the use of an implant (2) comprising a transponder coil (1) for introduction into an eye (6) for determining an intraocular pressure for the objective measurement of the boundaries of a field of vision is proposed.

14 Claims, 6 Drawing Sheets

(51) Int. Cl.
　　*A61B 3/113*　　　　(2006.01)
　　*A61B 3/12*　　　　(2006.01)
　　*A61B 3/16*　　　　(2006.01)
　　*G16H 50/30*　　　(2018.01)

(58) Field of Classification Search
　　CPC ........... A61B 3/14; A61B 3/103; A61B 3/024;
　　　　　　　A61B 3/032; A61B 3/18; A61B 3/1015
　　USPC ....... 351/205, 200, 209, 210, 221, 222, 245,
　　　　　　　　　　　351/246, 206, 211, 223
　　See application file for complete search history.

(56)　　　　　　References Cited

U.S. PATENT DOCUMENTS

| | | | |
|---|---|---|---|
| 2007/0236213 A1* | 10/2007 | Paden | A61B 3/16 |
| | | | 324/228 |
| 2009/0076367 A1* | 3/2009 | Sit | A61B 3/16 |
| | | | 600/398 |
| 2009/0207378 A1* | 8/2009 | Ito | A61B 3/165 |
| | | | 351/245 |
| 2015/0342723 A1 | 12/2015 | Abramson et al. | |
| 2016/0128587 A1* | 5/2016 | Kuenen | A61B 3/1241 |
| | | | 600/561 |
| 2017/0365101 A1* | 12/2017 | Samec | G06T 19/006 |

| | | | |
|---|---|---|---|
| 2019/0282094 A1* | 9/2019 | Lamrani | B29D 11/0073 |
| 2019/0344076 A1* | 11/2019 | Irazoqui | G02C 7/04 |
| 2021/0271320 A1* | 9/2021 | Fiess | G02B 27/0093 |

FOREIGN PATENT DOCUMENTS

| | | |
|---|---|---|
| JP | 2005137910 A | 6/2005 |
| JP | 2014516290 A | 7/2014 |
| JP | 2017037329 A | 2/2017 |
| WO | 2011035262 A1 | 3/2011 |
| WO | 2012136431 A1 | 10/2012 |
| WO | 2014110190 A2 | 7/2014 |
| WO | 2015008654 A1 | 1/2015 |

OTHER PUBLICATIONS

CN102711594A Espacenet english abstract, published Oct. 3, 2012, p. 1.

U.S. Pat. No. 2014016097A1 abstract, Espacenet English abstract for related application JP2014516290, published Jan. 16, 2014, p. 1.

CN103458775A Espacenet english abstract, published Dec. 18, 2013, p. 1.

JP2005137910A Espacenet english abstract, published Jun. 2, 2005, p. 1.

JP2017037329A Espacenet english abstract, published Feb. 16, 2017, p. 1.

* cited by examiner

AMENDED
Fig.4
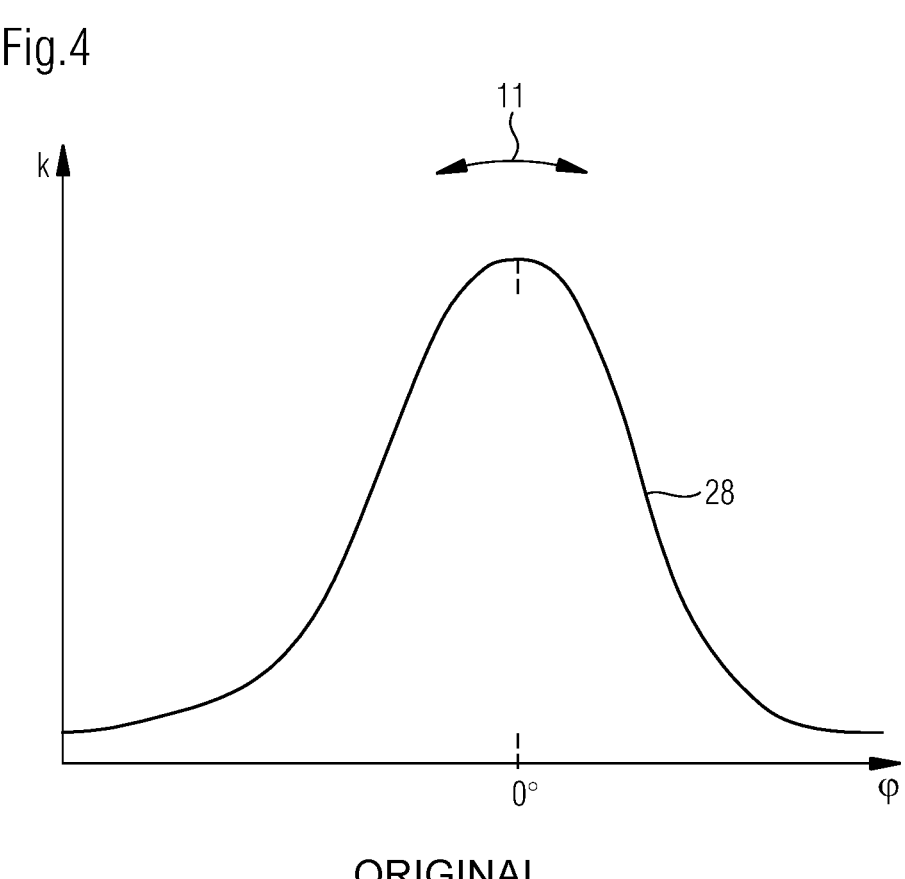
ORIGINAL

ARRANGEMENT AND METHOD FOR MEASURING A FIELD OF VISION AND USE OF AN IMPLANT

FIELD OF INVENTION

The present invention relates to an arrangement and a method for measuring a field of vision of an eye.

BACKGROUND

The present invention further relates to a use of an implant comprising a transponder coil for introduction into an eye for determining an intraocular pressure for the objective measurement of boundaries of a field of vision.

A field of vision of an eye is currently measured by means of perimetry. Optical stimuli are presented one after the other at different locations in front of the eye. The subjective perception of these stimuli is recorded depending on their location and their strength. A basic distinction is to be made between static and kinetic examination methods. In the former, the stimuli are presented at fixed locations and their intensity increased or decreased until the person examined signals a perception or no longer signals it. In the latter, stimuli that are invariable in their intensity are moved from outside the field of vision boundaries into the assumed field of vision and the location of the perception is viewed as the boundary of the field of vision for the given stimulus intensity.

This method can generally only be used when person examined cooperates well and the person to be examined has to visit a trained specialist who will carry out the measurement. In addition, the person to be examined must visit a doctor's practice having appropriate measuring systems.

Against this background, the present invention is based on the object of specifying an arrangement of the type mentioned above, and a method of the type mentioned above, which, while avoiding certain disadvantages, enable an objective, less complex and more reliable measurement of a field of vision of an eye.

SUMMARY

According to the invention, this objective is achieved with regard to the arrangement with a generic arrangement which comprises measuring means for measuring eye movement. This is based on the medical knowledge that the parameters of eye movement, such as amplitude and frequency, provide information about the field of vision. This opens up the possibility of continuous measurement of the field of vision of the eye outside of an ophthalmological practice, so that the effort for the patient is reduced. In addition, the measurements can be made at shorter time intervals, which enables better monitoring of the disease progression.

In an advantageous configuration of the invention, the measuring means comprise a transponder coil for introduction into the eye. This means that the effort for patients who have already had an implant with a transponder coil inserted into their eyes is very low. This is particularly the case for special implants for measuring intraocular pressure. These patients do not have to undergo any additional intervention to enable the advantages of an objective measurement of the field of vision. In addition, no complex optics is required to detect eye movement.

In an additional embodiment of the invention, the measuring means comprise a reading coil for attachment at a distance from the transponder coil in front of the eye. This means that no complex optics are required to detect eye movement and the person to be examined can carry out the measurement independently without the support of a trained specialist. This enables monitoring over a longer period of time and changes in the field of vision due to illness can be detected more quickly.

An advantageous embodiment of the invention comprises storage means for storing the measured parameters of the eye movement. This means that the measured data can be evaluated over a longer period of time. Everyday random eye movements can be observed over a longer period of time. The continuous fixation of the eye to be examined on a central point is no longer necessary. This constitutes a considerable improvement in the measurement method, since the results are not dependent on the cooperation of the patient and are therefore more comparable. This is an enormous advantage, particularly for the treatment of glaucoma, since the treatment of glaucoma requires regular monitoring of visual performance and, above all, its development over time and the extent of defects in the field of vision.

An advantageous embodiment of the invention comprises data transmission means for transmitting the measured parameters of the eye movement to the storage means. This means that the data can also be read and interpreted remotely by a trained specialist, without the person being examined having to visit the ophthalmological practice. This minimizes the effort on the part of the patient. Furthermore, this is advantageous for a telemedicine-oriented approach to the treatment of glaucoma.

An advantageous embodiment of the invention comprises an implant for determining an intraocular pressure. This makes the effort for patients who already have a generic implant implanted in the eye extremely low. No additional medical intervention is required. The second coil, which can be mounted in front of the eye, for example, on glasses, is easy to attach and affordable. The patient thus receives a system for measuring the field of vision which is easy to handle and portable. This gives the patient flexibility to schedule their day. The measurements no longer have to be carried out on a location-specific basis in an ophthalmological practice.

An advantageous embodiment of the invention comprises energy supply means for supplying energy for the transponder coil and/or the reading coil and/or for the measuring means and/or for the reading means and/or for the data transmission means and/or for the storage means and/or the implant. This enables location-independent, automatic and continuous measurement of the field of vision. After a briefing, the patient is able to carry out the measurement independently and thus ensure monitoring of the eye and glaucoma damage and/or field of vision disorders.

According to the invention, the object with regard to the objective, less complex and more reliable measuring of a field of vision of an eye is achieved through the use of an implant that can be introduced into an eye, preferably designed for determining an intraocular pressure and that has a transponder coil, to objectively measure the boundaries of a field of vision. This enables a field of vision of an eye to be measured automatically and continuously, independently of the patient's participation. The patient does not have to rely on the presence of a trained specialist to carry out the measurement, rather, said measurement can be carried out independently after receiving instruction from said specialist. The changes in the parameters due to the minimal, very rapid movement of the eye can thus be measured. This enables detection of the slightest eye movements, from which the boundaries of the field of vision can be determined.

According to the invention, the object of the objective, less complex and more reliable measurement of a field of vision of an eye with regard to the method is achieved using a method of the generic type with which an eye movement is measured. This enables conclusions to be drawn about glaucoma damage and/or field of vision disorders via the relationship with rapid eye movement, which is also known as saccadic movement.

In a preferred embodiment of the invention, at least one amplitude and/or one frequency of the eye movement is measured, preferably in a time-resolved manner. This enables conclusions to be drawn about the field of vision of the examined person, insofar as the amplitude of the eye movement of an eye that has glaucoma damage is smaller compared to the amplitude of the eye movement of an eye that does not have glaucoma damage. The time-resolved measurement makes it possible to determine changes over a period of time and thus ensure better treatment of glaucoma. This constitutes an important improvement in the treatment of glaucoma.

In an additional embodiment of the invention, a transponder coil is introduced into the eye. This enables continuous measurement of eye movement outside of an ophthalmological practice. Patients who already have an implant to measure intraocular pressure do not have to undergo any additional medical intervention, since the implant can be used to measure eye movement.

In an advantageous embodiment of the invention, a reading coil for determining parameters of the eye movement is arranged at a defined reference point to the transponder coil outside the eye. This means that no additional, complex optics for measuring is required on the part of the patient. This provides an easy-to-use and transportable system for measuring the field of vision, which the patient can operate independently after instruction.

In an additional embodiment of the invention, a high frequency current is sent through the reading coil. The generation of a magnetic flux between the transponder coil and the reading coil is triggered externally. This enables conclusions to be drawn about glaucoma damage and/or field of vision disorders via the parameters of the magnetic flux (amplitude and frequency). It is advantageous in this case that the measurements are carried out objectively and that the patient does not need to cooperate. The patient does not have to be exposed to any additional visual stimuli. Everyday random movements of the eye can be measured. This constitutes considerable relief for the patient, who does not have to visit an ophthalmological practice for the necessary measurements.

In an advantageous embodiment of the invention, the parameters of the eye movement are measured again in a comparative measurement after a freely definable time. This enables continuous monitoring at short time intervals, for example, on an hourly or daily basis, with regard to changes in the field of vision of a patient. This enables a better response to changes, which constitutes a significant improvement in the treatment of glaucoma.

In an advantageous embodiment of the invention, changes in the measured parameters of the eye movement of an initial measurement and the parameters of the comparative measurement are evaluated after a freely definable time. In this way, conclusions can be drawn about glaucoma damage and/or field of vision disorders via the changes in the parameters. The measurements can be triggered independently by the patient and the changes in the measured parameters can be evaluated via an algorithm. This enables a telemedicine-oriented approach to the treatment of glaucoma. The active participation of the patient in measuring the parameters is thus no longer necessary, which makes the method safer and the measurement results more comparable.

In an additional embodiment of the invention, the field of vision of the eye and/or changes over time in the field of vision of the eye are determined on the basis of changes in the parameters. This enables an objective measurement of the field of vision outside of an ophthalmological practice. This enables the data to be measured over a longer period of time, which in turn enables a precise analysis of the measurement data and, associated therewith, a detection of changes in, for example, the average speed and/or amplitude of the eye movement.

In an advantageous embodiment of the invention, movements of the head relative to the eye are determined by means of an additional sensor, particularly an acceleration and/or position sensor. This enables better data quality to be obtained for the measured parameters of the eye movement through the detection of movement artifacts. This enables evaluation via an algorithm or an artificial intelligence system.

BRIEF DESCRIPTION OF THE DRAWINGS

The invention is described by way of example in a preferred embodiment with reference to a drawing, further advantageous details being shown in the figures of the drawing.

Functionally identical parts are thereby labeled with the same reference numerals.

In the figures in the drawing, in detail:

Figure 1:
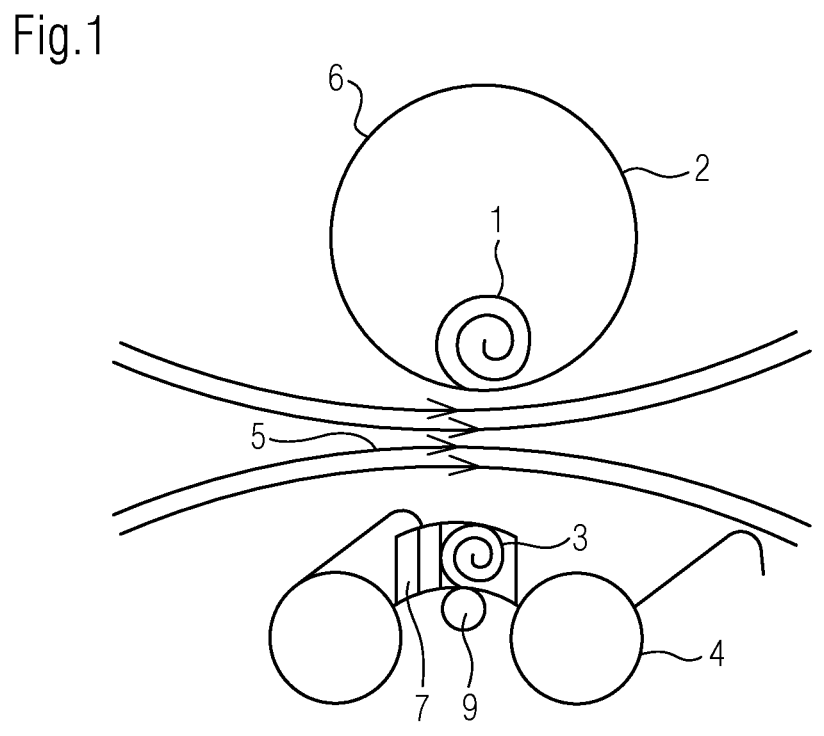
Figure 1A:
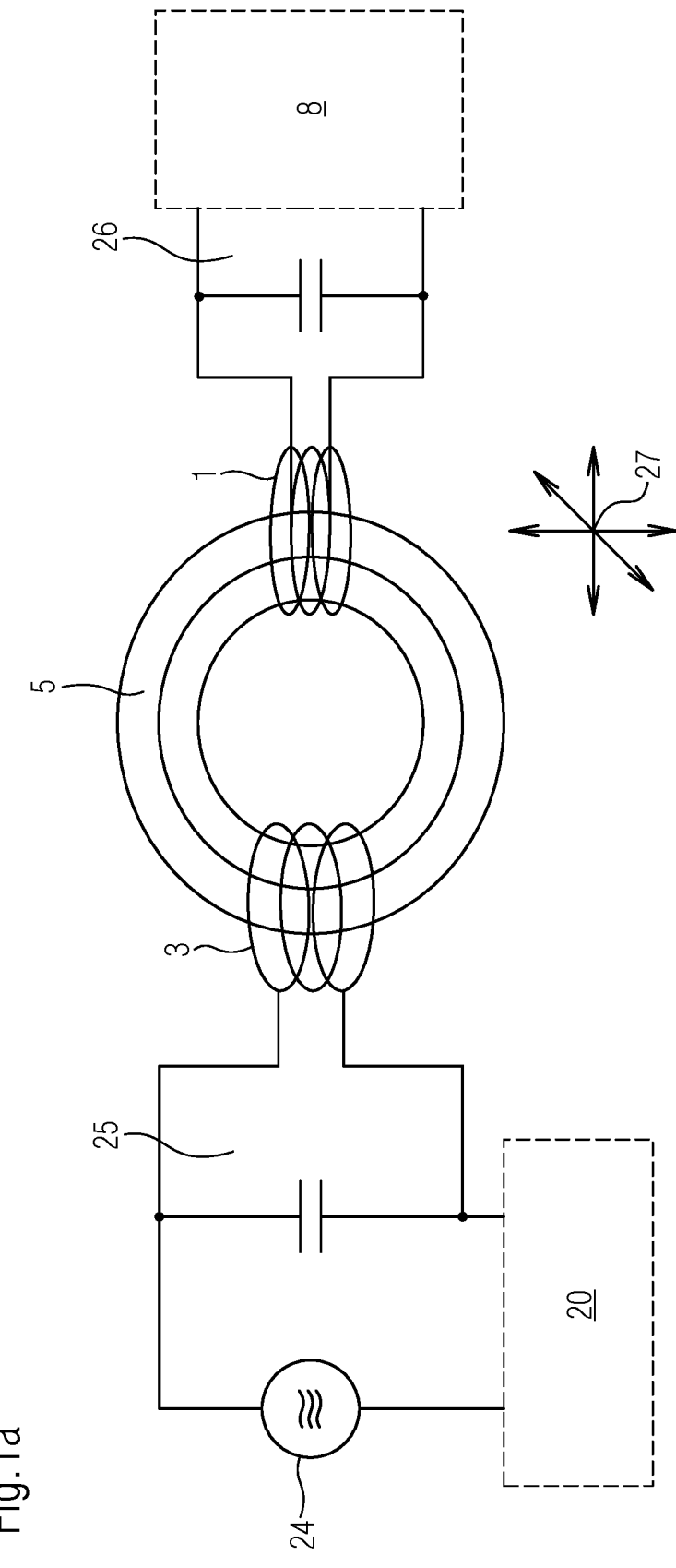
Figure 3:
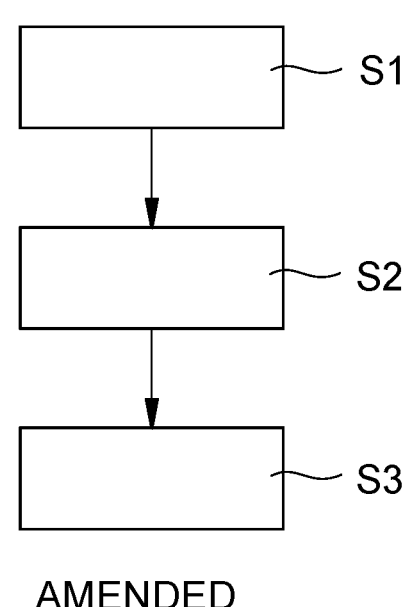
Figure 5:
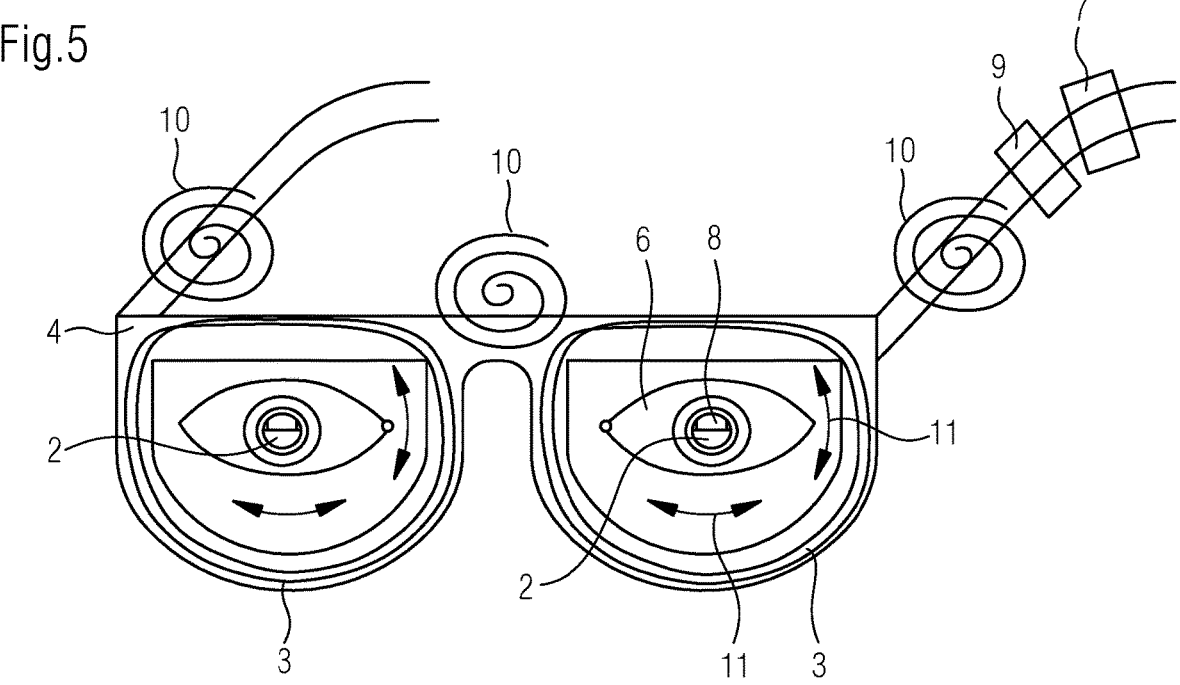
Figure 6:
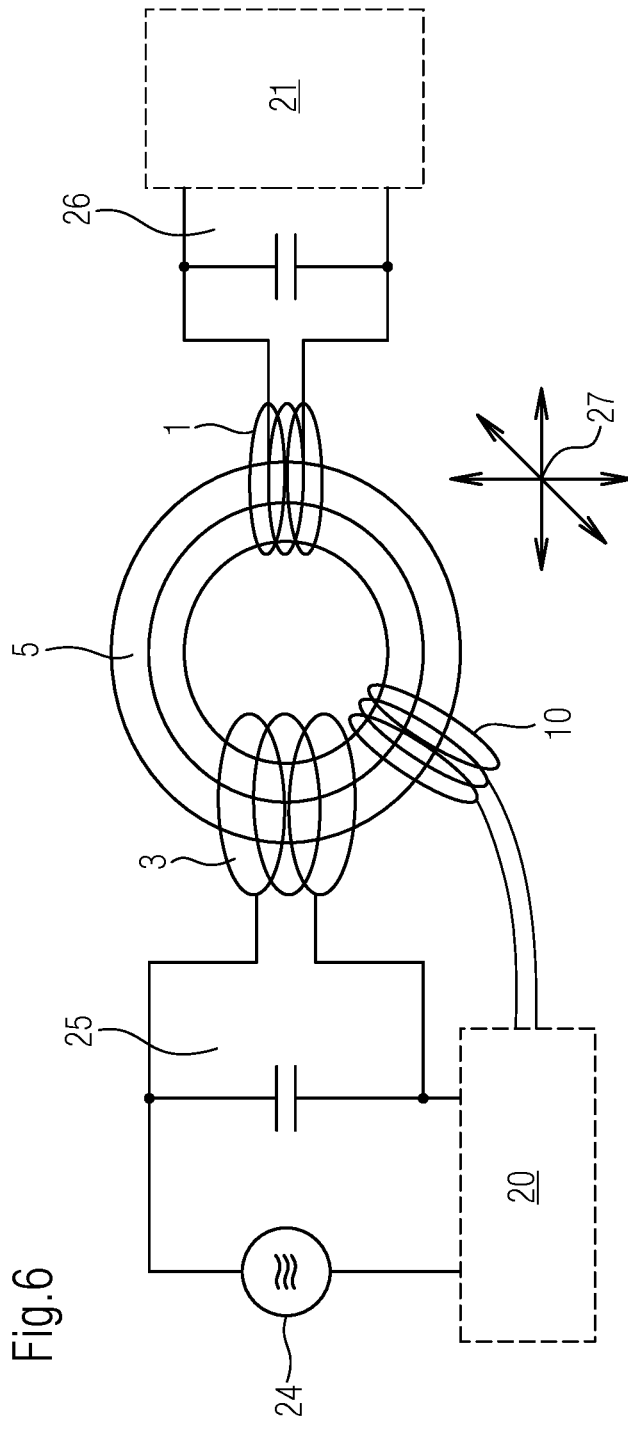

FIG. 1: shows schematically and not to scale, an arrangement of a transponder coil on an implant for determining the intraocular pressure and a reading coil in front of the eye, fastened to glasses and the induced magnetic field, according to an embodiment of the invention;

FIG. 1a: shows the structure of the electronics in an arrangement of glasses having reading coils for sending and receiving a signal;

Figure 2:
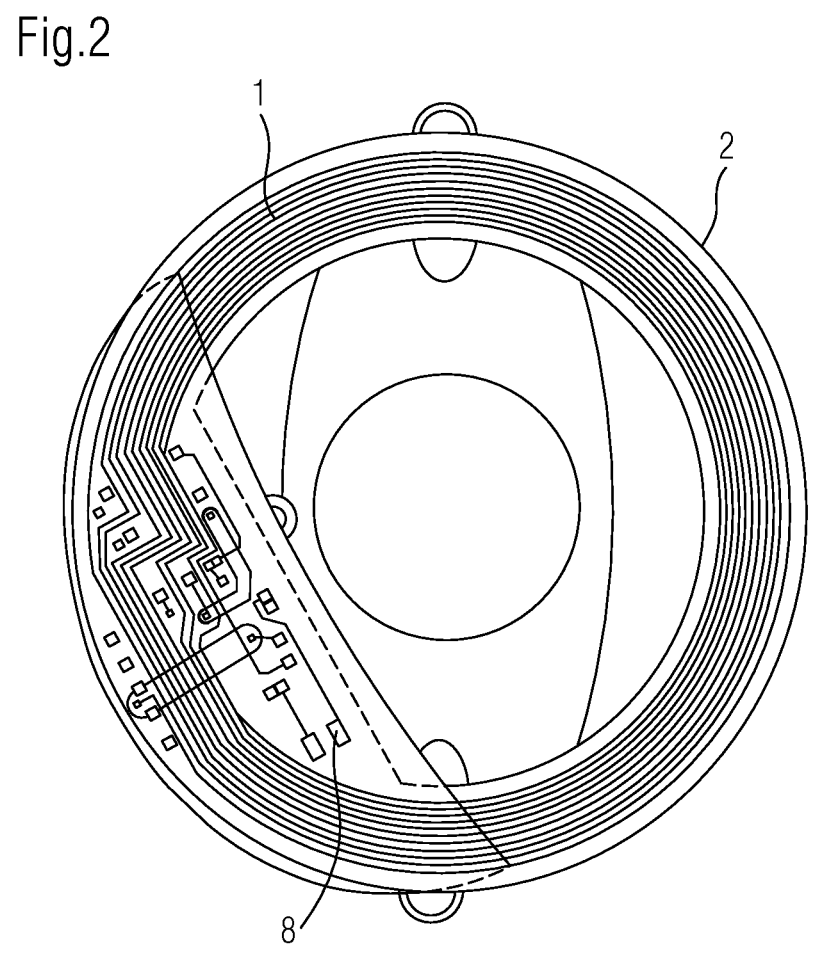

FIG. 2: shows a schematic representation of an implant for determining the intraocular pressure using a transponder coil, according to an embodiment of the invention;

FIG. 3: shows a flowchart for illustrating the method for determining the changes in the field of vision, according to an embodiment of the invention;

FIG. 4: shows schematically, the change in the coupling between the electromagnetically coupled coils as a function of the angle $\varphi$ of the eye movement;

FIG. 5: shows a schematic representation of an arrangement of glasses having separate receiving coils in front of the eye;

FIG. 6: shows the structure of the electronics in an arrangement of glasses having a separate receiving coil.

DETAILED DESCRIPTION

FIG. 1 illustrates schematically the arrangement of a transponder coil 1 on an implant 2 for determining the intraocular pressure and a reading coil 3 at a defined point in front of the eye, for example, fastened to glasses 4, and the induced magnetic field 5. The implant 2, which integrates the transponder coil 1, acts like a passive transponder, that is, it is switched on as soon as the energy induced by the magnetic flux is sufficient for operation. A current sent through the reading coil 3, for example, a high-frequency current, generates a magnetic flux. This creates a weak coupling between the two coils, the intensity of which is changed by minimal movement of the eye 6 in which the transponder coil 1 is implanted. The parameters of the magnetic flux are read out by a reading coil 3.

An intraocular pressure sensor 2 is implanted in the eye 6 of the patient and is used there to regularly measure the intraocular pressure and, associated therewith, to treat glaucoma. For this purpose, the glasses 4 are always arranged in front of the eye 6 of the patient and the intraocular pressure is measured continuously. For example, pressure profiles of several hours or days are recorded. In the same way, according to the invention, changes in the field of vision can be recorded using the arrangement shown in FIG. 1.

FIG. 1 further shows that the reading coil 3 is arranged in a miniaturized package with an accumulator and/or a battery 7 for providing energy for the transponder coil 1 and the reading coil 3 on the glasses 4.

To improve data quality, it may be necessary to determine the movements of the head relative to the eye using an additional 3D-acceleration and/or position sensor 9.

FIG. 1a shows the structure of the electronics in an arrangement of glasses having reading coils 3. In this arrangement, the reading coil 3 is used both for receiving and sending a signal. A separate coil for receiving the signal is not required, since the reading coil 3 operates in a broadband range that is sufficient for both sending and receiving.

As can be seen from FIG. 1a, a high-frequency generator 24 is connected to the reading coil 3. Said high-frequency generator 24 generates a high-frequency current which is sent through the reading coil 3, generating a magnetic flux there. This creates an oscillating circuit 25 on the side of the reading coil 3. The transponder oscillating circuit 26 on the side of the transponder coil 1 functions like a passive oscillating circuit. Evaluation electronics is also connected to the high-frequency generator 24 in order to be able to detect the slightest movements 27 of the eyes in all spatial axes.

The microchip 8, which is inactive while the measurement is being carried out, is connected to the transponder coil 1.

FIG. 2 shows a schematic representation of an implant for determining the intraocular pressure 2 using a transponder coil 1. Furthermore, a microchip 8 is arranged on the intraocular pressure sensor 2, which microchip is fed to carry out the measurement such that its working threshold has not yet been reached and the implant 2 functions like a passive oscillating circuit.

Only the reading coil 3 is minimally excited to carry out the measurement of the eye movement, so that a sufficient field strength is available to operate the implant 2. For this purpose, an external signal must be given, for example, from the person to be examined, so that a current is induced in the transponder coil. A weak coupling thus arises between the transponder coil 1 and the reading coil 3, the intensity of which is changed by minimal movement of the eye in which the transponder coil 1 is implanted. The microchip 8 is inactive for carrying out the measurement.

The transponder coil 1 shown in FIG. 2 does not necessarily have to be arranged on a system 2 to be implanted in the eye, but can also be integrated in contact lenses within the scope of the invention.

FIG. 3 shows a flowchart of the method for determining the changes in the field of vision according to an embodiment of the invention. The parameters of the field of vision are determined and stored in an initial measurement S1. After a freely definable time t, a comparative measurement S2 is carried out and the parameters of the field of vision are determined again. The results are then compared with one another and evaluated using an algorithm or artificial intelligence. An evaluation S3 of the parameters takes place. The changes in the amplitude and frequency of the eye movement are associated with field of vision disorders or glaucoma damage.

FIG. 4 shows the electromagnetic coupling k 28 of the reading coil 3 and the transponder coil 1, which is arranged on the implant 2. The electromagnetic coupling 28 changes as a function of the slightest movements of the eye 11. The movements of the eye 11 are illustrated in FIG. 4 as an angle $\varphi$. The angle $\varphi$ is the torsion angle of the eye in all three spatial axes. As shown in FIG. 4, the coupling 28 is at a maximum at an angle $\varphi=0°$ and decreases as a function of the angle $\varphi$. The change in the coupling of the reading coil 3 and the transponder coil 1 is recorded and evaluated.

FIG. 5 shows an arrangement of glasses having separate receiving coils 10. In such an arrangement, the signal is sent by the reading coil 3 and retrieved by the separate receiving coils 10. As a result, the reading coil 3 can be designed with a narrower band. In addition, the position and alignment of the implant 2 and thus the slightest movements 27 of the eye can be detected by means of a triangulation to further improve the quality of the data.

The functioning of the arrangement as illustrated in FIG. 5 is identical to the functioning of the arrangement as illustrated in FIG. 1a.

FIG. 6 shows the structure of the electronics in an arrangement of glasses having separate receiving coils 10. In this arrangement, the signal is sent by the reading coil 3 and retrieved by the separate receiving coils 10. The receiving coil 10 is coupled to the evaluation electronics 20 so that the received signals can be stored and evaluated.

Apart from the additional receiving coil 10, the structure of the electronics is identical to the structure of the electronics of the arrangement of glasses having reading coils 3, as illustrated in FIG. 1a.

LIST OF REFERENCE NUMERALS

1 transponder coil
2 intraocular pressure sensor
3 reading coil
4 glasses
5 induced magnetic field
6 eye
7 accumulator and/or battery
8 microchip
9 3d-acceleration and/or position sensor
10 receiving coil
11 eye movement
20 evaluation electronics
24 high frequency generator
25 oscillating circuit
26 transponder oscillating circuit
27 eye movement
28 electromagnetic coupling
S1 initial measurement
S2 comparative measurement
S3 evaluation of the parameters

The invention claimed is:
1. An apparatus for measuring a field of vision of an eye (6) and changes over time in the field of vision comprising:

a measuring means (1, 3) configured to measure a measured parameter of an eye movement, including at least one amplitude and one frequency of the eye movement in a time-resolved manner, to measure the field of vision and the changes over time in the field of vision and the measuring means comprises a transponder coil (1) for introduction into the eye (6) and a reading coil (3) for attachment at a distance from the transponder coil (1) in front of the eye (6);

the measuring means (1, 3) has an additional sensor (9) configured to determine movements of a head relative to the eye (6);

wherein the reading coil (3) is fastened to glasses (4) at a defined reference point to the transponder coil (1) outside and in front of the eye (6); and wherein the transponder coil (1) is integrated into contact lenses that are placed on the eyes (6) or implants (2) introduced into the eyes (6).

2. The apparatus according to claim 1, comprising a storage means configured to store the measured parameters of the eye movement.

3. The apparatus according to claim 2, further comprising a data transmission means for transmitting the measured parameters of the eye movement to the storage means.

4. The apparatus according to claim 1, wherein the implant (2) is configured to measure an intraocular pressure of the eye (6).

5. The apparatus according to claim 1, wherein changes in the field of vision of the eye (6) and/or changes over time in the field of vision of the eye (6) are determined based on the changes in the measured parameters.

6. The apparatus according to claim 3, further comprising the implant (2) for determining an intraocular pressure of the eye (6).

7. The apparatus according claim 6, further comprising an energy supply means (7) for providing energy for the transponder coil, the reading coil, for the measuring means (1, 3), for a reading means, for the data transmission means, for the storage means and/or the implant (2).

8. The apparatus according to claim 1, wherein the measured parameter of eye movement is continuously monitored at short time intervals.

9. A method of measuring the health of an eye (6) comprising:

measuring an intraocular pressure of the eye (6) with an implant (2) introduced into the eye (6), wherein the implant (2) has a transponder coil (1), and a reading coil (3), wherein the reading coil (1) is fastened to glasses (4) at a defined reference point to the transponder coil (1) outside and in front of the eye (6);

measuring boundaries of a field of vision and changes over time in the field of vision based on an amplitude and frequency of an eye movement measured in a time-resolved manner using the implant; and movements of a head relative to the eye (6) by an additional sensor.

10. A method for measuring a field of vision of an eye (6) and changes over time in the field of vision comprising:

Introducing a transponder coil (1) into the eye (6) and a reading coil (3) is attached at a distance from the transponder coil (1) in front of the eye (6), wherein an intensity of a coupling between the transponder coil (1) and the reading coil (3) is changed by minimal movement of the eye (6), and wherein the change of the coupling of the reading coil and the transponder coil is recorded and evaluated;

measuring parameter of an eye movement, including at least one amplitude and one frequency of the eye movement are measured in a time-resolved manner to measure the field of vision and the changes over time in the field of vision;

measuring movements of a head relative to the eye (6) by an additional sensor (9); and wherein the reading coil (3) is fastened to glasses (4) at a defined reference point to the transponder coil (1) outside and in front of the eye (6); and wherein the transponder coil (1) is integrated into contact lenses that are placed on the eye (6) or implants (2) introduced into the eyes (6).

11. The apparatus according to claim 10, wherein a high-frequency current is sent through the reading coil (3).

12. The method according to claim 10, further comprising measuring the eye movement again after a freely definable time; and determining a comparative measurement (S2).

13. The method according claim 9, wherein the additional sensor (9), comprises an acceleration and/or position sensor (9).

14. The method according to claim 10, further comprising:

measuring and storing parameters of the eye movement as an initial measurement (S1); and measuring the parameters of the eye movement for a comparative measurement (S2) after a freely definable time.

\* \* \* \* \*